United States Patent
Ringold et al.

(10) Patent No.: US 8,521,557 B1
(45) Date of Patent: *Aug. 27, 2013

(54) SYSTEM AND METHODS FOR PROCESSING REJECTED HEALTHCARE CLAIM TRANSACTIONS FOR OVER-THE-COUNTER PRODUCTS

(75) Inventors: James Morgan Ringold, Lawrenceville, GA (US); Roger Pinsonneault, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 228 days.

This patent is subject to a terminal disclaimer.

(21) Appl. No.: 12/982,395

(22) Filed: Dec. 30, 2010

Related U.S. Application Data

(63) Continuation-in-part of application No. 12/140,015, filed on Jun. 16, 2008, now Pat. No. 8,036,918.

(51) Int. Cl.
*G06Q 50/00* (2012.01)

(52) U.S. Cl.
USPC .............................................................. 705/2

(58) Field of Classification Search
USPC ....................................... 705/2, 30; 235/379
See application file for complete search history.

(56) References Cited

U.S. PATENT DOCUMENTS

| | | |
|---|---|---|
| 5,628,530 A | 5/1997 | Thornton |
| 6,012,035 A | 1/2000 | Freeman, Jr. et al. |
| 6,112,182 A | 8/2000 | Akers et al. |
| 6,595,342 B1 | 7/2003 | Maritzen et al. |
| 6,726,092 B2 | 4/2004 | Goldberg et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,337,129 B1 | 2/2008 | Lowry et al. |
| 7,346,768 B2 | 3/2008 | DiRienzo |
| 7,409,632 B1 | 8/2008 | DiRienzo |
| 7,734,483 B1 | 6/2010 | Smith et al. |
| 7,783,383 B2 | 8/2010 | Eliuk et al. |

(Continued)

FOREIGN PATENT DOCUMENTS

| | | |
|---|---|---|
| CA | 2482370 A1 | 3/2006 |
| WO | WO 9106917 A1 | 5/1991 |

(Continued)

OTHER PUBLICATIONS

"Pharmacy Reject Codes" NCPDP.*

(Continued)

*Primary Examiner* — John Pauls
(74) *Attorney, Agent, or Firm* — Sutherland Asbill & Brennan LLP

(57) ABSTRACT

Systems and methods for processing rejected healthcare claim transactions for over-the-counter ("OTC") products are provided. A healthcare claim transaction associated with a product requested by a customer may be received from a healthcare provider computer. The healthcare claim transaction may be communicated to a claims processor for adjudication, and a denied claim response for the healthcare claim transaction may be received from the claims processor. Based at least in part upon a classification of the product, the denied claim response may be converted to an approved claim response, and the approved claim response may be communicated to the healthcare provider computer. In certain embodiments, the above operations may be performed by one or more computers associated with a service provider.

20 Claims, 5 Drawing Sheets

(56) References Cited

U.S. PATENT DOCUMENTS

| | | |
|---|---|---|
| 7,840,424 B2 | 11/2010 | Wiley et al. |
| 7,856,364 B1 | 12/2010 | Wiley et al. |
| 7,912,741 B1 | 3/2011 | Pinsonneault |
| 7,921,021 B1 | 4/2011 | Newman |
| 8,036,918 B1 | 10/2011 | Pinsonneault |
| 8,050,943 B1 | 11/2011 | Wiley et al. |
| 2002/0002495 A1 | 1/2002 | Ullman |
| 2002/0032582 A1 | 3/2002 | Feeney et al. |
| 2002/0035484 A1 | 3/2002 | McCormick |
| 2002/0087583 A1 | 7/2002 | Morgan et al. |
| 2002/0111832 A1 | 8/2002 | Judge |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0074234 A1 | 4/2003 | Stasny |
| 2003/0097310 A1 | 5/2003 | Ono et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0039599 A1 | 2/2004 | Fralic |
| 2004/0073456 A1 | 4/2004 | Gottlieb et al. |
| 2004/0073457 A1 | 4/2004 | Kalies |
| 2004/0078234 A1 | 4/2004 | Tallal, Jr. |
| 2004/0088187 A1 | 5/2004 | Chudy et al. |
| 2004/0103062 A1 | 5/2004 | Wood et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0199545 A1 | 10/2004 | Wagner et al. |
| 2004/0236630 A1 | 11/2004 | Kost et al. |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0080692 A1* | 4/2005 | Padam et al. .................. 705/30 |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240442 A1 | 10/2005 | Lapsker et al. |
| 2005/0240473 A1 | 10/2005 | Ayers, Jr. et al. |
| 2005/0261939 A1 | 11/2005 | Augspurger et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0085231 A1 | 4/2006 | Brofman |
| 2006/0113376 A1* | 6/2006 | Reed et al. .................. 235/379 |
| 2006/0149595 A1 | 7/2006 | Williams et al. |
| 2006/0149784 A1 | 7/2006 | Tholl et al. |
| 2006/0184391 A1 | 8/2006 | Barre et al. |
| 2006/0224443 A1 | 10/2006 | Soza et al. |
| 2006/0235747 A1 | 10/2006 | Hammond et al. |
| 2006/0259363 A1 | 11/2006 | Jhetam et al. |
| 2007/0005402 A1 | 1/2007 | Kennedy et al. |
| 2007/0043589 A1 | 2/2007 | Warren et al. |
| 2007/0050209 A1 | 3/2007 | Yered |
| 2007/0094133 A1 | 4/2007 | Anandarao et al. |
| 2007/0136100 A1 | 6/2007 | Daugherty et al. |
| 2007/0162303 A1* | 7/2007 | Wiley et al. .................. 705/2 |
| 2007/0185799 A1 | 8/2007 | Harrison et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0276697 A1 | 11/2007 | Wiley, II et al. |
| 2008/0033750 A1 | 2/2008 | Burriss et al. |
| 2009/0030719 A1 | 1/2009 | Nadas et al. |
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |

FOREIGN PATENT DOCUMENTS

| | | |
|---|---|---|
| WO | WO 9503569 A3 | 2/1995 |
| WO | WO 9725682 A1 | 7/1997 |
| WO | WO 9850871 A1 | 11/1998 |
| WO | WO 0039737 A1 | 7/2000 |
| WO | 03098401 A2 | 11/2003 |
| WO | WO 2007025295 A2 | 3/2007 |

OTHER PUBLICATIONS

Final Office Action for U.S. Appl. No. 12/560,071 mailed Nov. 8, 2012.

Non-Final Office Action for U.S. Appl. No. 12/555,589 mailed Dec. 9, 2011.

Marie Chisholm et al. "Pharmaceutical Manufacturer Assistance Program." Arch Intern Med. vol. 162, Apr. 8, 2002.

Non-Final Office Action for U.S. Appl. No. 12/140,015 mailed Oct. 8, 2010.

Non-Final Office Action for U.S. Appl. No. 12/956,411 mailed Jan. 24, 2011.

Final Office Action for U.S. Appl. No. 12/140,015 mailed Jan. 31, 2011.

Non-Final Office Action for U.S. Appl. No. 12/415,062 mailed Mar. 30, 2011.

Non-Final Office Action for U.S. Appl. No. 12/730,015 mailed Mar. 6, 2012.

Final Office Action for U.S. Appl. No. 12/555,589 mailed Apr. 11, 2012.

Non-Final Office Action for U.S. Appl. No. 12/560,071 mailed Jun. 21, 2012.

Non-Final Office Action for U.S. Appl. No. 12/570,982 mailed Jun. 20, 2012.

Final Office Action for U.S. Appl. No. 12/730,015 mailed Aug. 14, 2012.

Notice of Allowance for U.S. Appl. No. 12/140,015 mailed Jun. 10, 2011.

Notice of Allowance for U.S. Appl. No. 12/956,411 mailed Aug. 5, 2011.

Final Office Action for U.S. Appl. No. 12/415,062 mailed Oct. 6, 2011.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britian's Traditionally Cautious National Health Service is Starting Trials for Online Prescriptions, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005.
www.ncoil.org/news/DrugCards2.doc dated Apr. 2002.
Non-final Office Action for U.S. Appl. No. 12/189,654 mailed Jan. 22, 2010.
Non-final Office Action for U.S. Appl. No. 12/189,650 mailed Jan. 22, 2010.
Notice of Allowance for U.S. Appl. No. 11/674,069 mailed Jul. 19, 2010.
Notice of Allowance for U.S. Appl. No. 12/189,650 mailed Aug. 13, 2010.
Notice of Allowance for U.S. Appl. No. 12/165,221 mailed Nov. 16, 2010.
Final Office Action for U.S. Appl. No. 12/570,982 mailed Jan. 17, 2013.
Opar, Alisa; "Rising drug costs prompt new uses for old pills." Nature Medicine, 12/1333 (2006).
Consalvo, Bob; "City of Bosont in the City Council" hearing notice, Dec. 6, 2006.
Almaro, Moshe; "Recovery and Reuse of Unused Prescription Drugs" MIT What Matters: Aug. 2005.
Strom, Stephanie; "Old Pills Finding New Medicine Cabinets" NY Times, May 18, 2005.
Siller et al., "Safe Disposal of Unused Controlled Substances" Avalere Health 2008.
Non-Final Office Action for U.S. Appl. No. 12/978,898 mailed Feb. 6, 2013.
Kaplan et al., "Let the Needles Do the Talking! Evaluating the New Haven Needle Exchange." Interfaces 23:1, Jan.-Feb. 1993 (pp. 7-26).
Final Office Action for U.S. Appl. No. 12/978,898 mailed May 16, 2013.

* cited by examiner

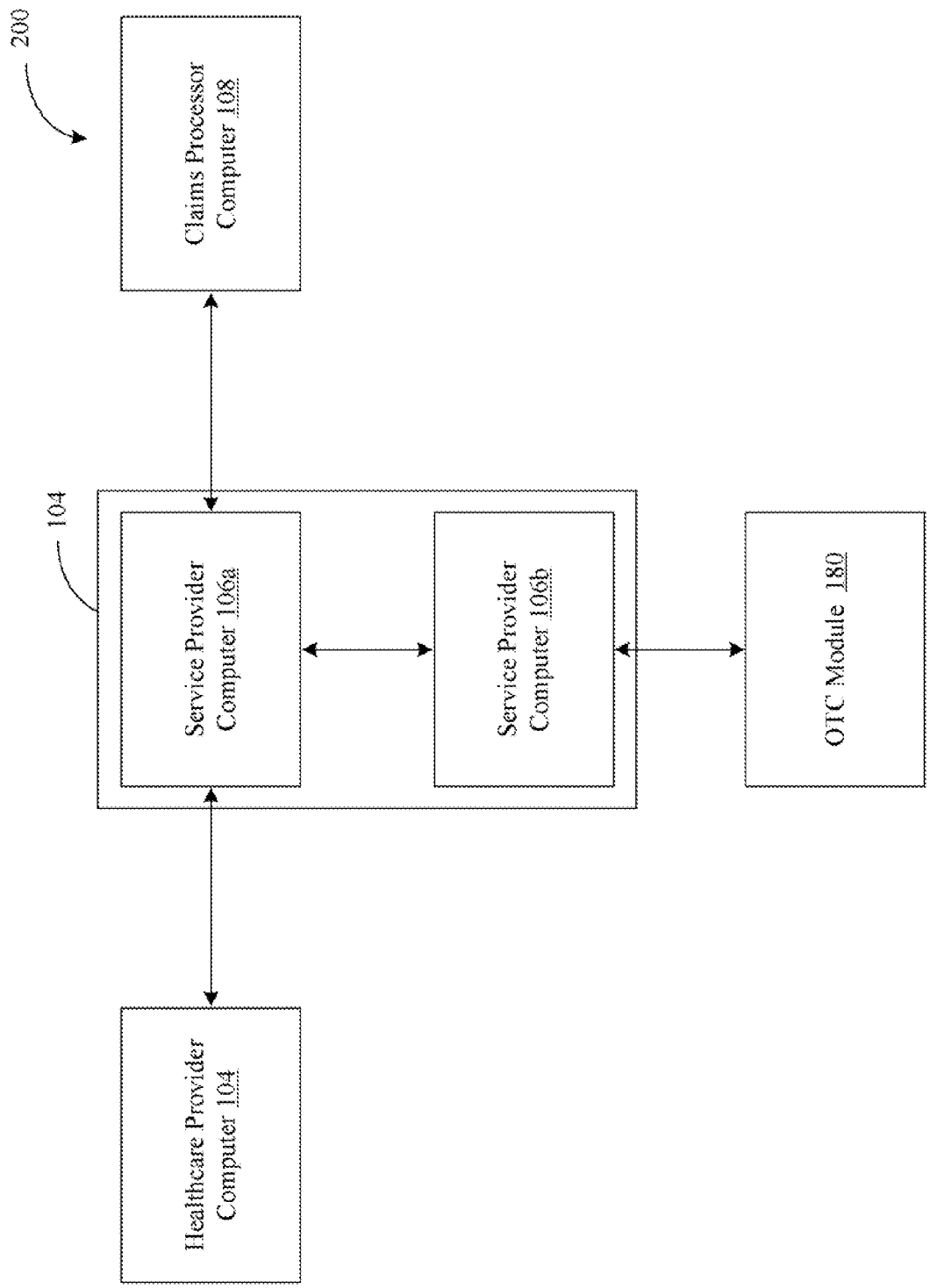

SYSTEM AND METHODS FOR PROCESSING REJECTED HEALTHCARE CLAIM TRANSACTIONS FOR OVER-THE-COUNTER PRODUCTS

CROSS-REFERENCE TO RELATED APPLICATION

This application is a continuation-in-part of co-pending U.S. patent application Ser. No. 12/140,015, filed Jun. 16, 2008, and entitled SYSTEMS AND METHODS FOR CONVERSIONS OF DENIED TRANSACTIONS THROUGH PATIENT FUNDING, the contents of which are incorporated by reference herein in their entirety.

FIELD OF THE INVENTION

Aspects of the invention relate generally to healthcare transactions, and more particularly, to processing rejected healthcare claim transactions for over-the-counter products.

BACKGROUND OF THE INVENTION

Healthcare providers, such as pharmacies, physicians, and/or hospitals, often generate healthcare claims or healthcare claim transactions that are communicated to appropriate claims processors or payors, such as insurance providers or government payors. It is relatively common for patients to receive prescriptions for over-the-counter ("OTC") medications and/or other OTC products. In these situations, a healthcare provider will typically submit healthcare claim transactions for the OTC products. While certain payors will approve healthcare claim transactions for OTC products, other payors will reject these claim transactions as being directed to uncovered products. These rejections may often lead to patients failing to complete the purchases for the OTC products, thereby resulting in missed opportunities and lost revenue for the healthcare providers. For example, a patient may be told that his/her healthcare claim transaction has been denied without the patient or healthcare provider realizing that the product is an OTC product. Therefore, systems and methods for processing rejected healthcare claim transactions for OTC products are desirable.

BRIEF DESCRIPTION OF THE INVENTION

Some or all of the above needs and/or problems may be addressed by certain embodiments of the invention. Embodiments of the invention may include systems, methods, and apparatus for processing rejected healthcare claim transactions for over-the-counter ("OTC") products. In one embodiment, a computer-implemented method for processing rejected healthcare claim transactions may be provided. A healthcare claim transaction associated with a product requested by a customer may be received from a healthcare provider computer. The healthcare claim transaction may be communicated to a claims processor for adjudication, and a denied claim response for the healthcare claim transaction may be received from the claims processor. Based at least in part upon a classification of the product, the denied claim response may be converted to an approved claim response, and the approved claim response may be communicated to the healthcare provider computer. In certain embodiments, the above operations may be performed by one or more computers associated with a service provider.

In accordance with another embodiment of the invention, a system for processing rejected healthcare claim transactions may be provided. The system may include at least one memory, and at least one processor. The at least one memory may be operable to store computer-executable instructions. The at least one processor may be configured to access the at least one memory and execute the computer-executable instructions to: receive, from a healthcare provider computer, a healthcare claim transaction associated with a product requested by a customer; direct communication of the healthcare claim transaction to a claims processor for adjudication; receive, from the claims processor, a denied claim response for the healthcare claim transaction; convert, based at least in part upon a classification of the product, the denied claim response to an approved claim response; and direct communication of the approved claim response to the healthcare provider computer.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein:

FIGS. 2A-2B are block diagrams of example data flows for processing claim transactions for over-the-counter products that are processed through a service provider, according to illustrative embodiments of the invention.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems, methods, and apparatus for processing rejected or denied healthcare claim transactions for over-the-counter ("OTC") products. In one example embodiment, a service provider may facilitate the routing or communication of a healthcare claim transaction between a healthcare provider and a claims processor. Following an adjudication of the healthcare claim transaction by the claims processor, a denied claim response for the healthcare claim transaction may be received by the service provider from the claims processor. The denied claim response may be evaluated and/or analyzed, and a determination may be made that a product associated with the denied healthcare claim transaction is an OTC product. For example, one or more product identifiers may be evaluated in order to determine that the product is an OTC product. As another example, one or more rejection codes may be evaluated in order to determine reasons for the denial or rejection of the healthcare claim transaction. Based at least in part upon the determination or identification of the product as an OTC product, the denied claim response may be converted into an approved claim response. The approved claim response may then be routed or otherwise communicated to the healthcare provider by the service provider. Additionally, as desired, a financial record of the conversion may be stored.

In certain embodiments, a price for the product may be calculated and included in the converted claim response. For example, a product identifier may be utilized to access and/or otherwise obtain pricing parameters for the product. A price for the product may then be calculated utilizing the pricing parameters and/or product quantity information. As desired, one or more available discounts and/or alternative sources of funding may also be determined. Available discounts and/or alternative funding may then be applied in order to reduce the calculated price. Once calculated or determined, the price may be utilized to modify various parameters (e.g., pricing fields) of the converted claim response. For example, a patient responsible amount may be modified to reflect the calculated price.

System Overview

Figure 1:
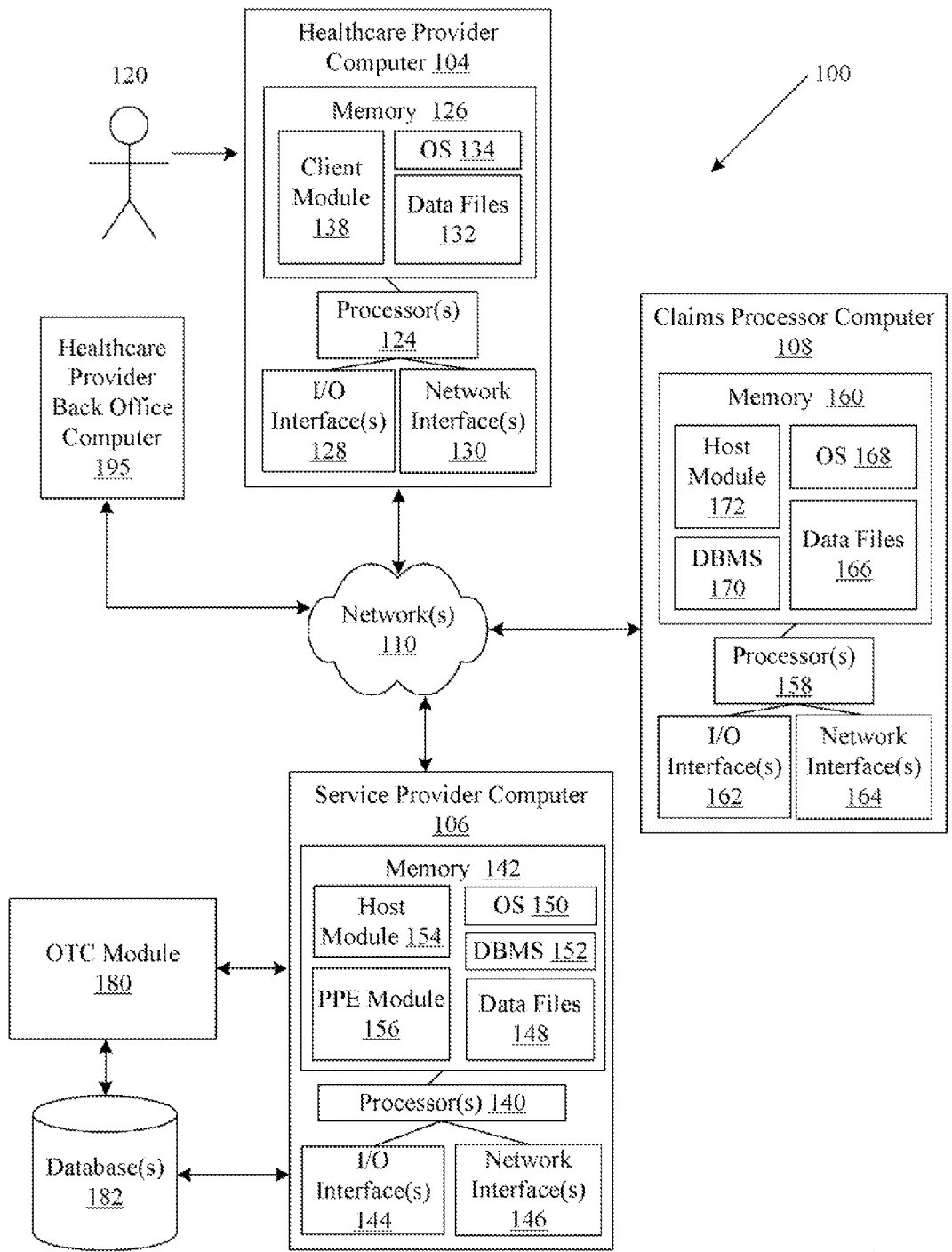
FIG. 1 illustrates an example overview of a system that facilitates the processing of claim transactions for over-the-counter products, according to an example embodiment of the invention.

An example system 100 that facilitates the processing of claim transactions for over-the-counter products will now be described illustratively with respect to FIG. 1. As shown in FIG. 1, the system 100 may include at least one healthcare provider computer 104, at least one service provider computer 106, and at least one claims processor computer 108. As desired, each of the healthcare provider computer 104, service provider computer 106, and/or claims processor computer 108 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with an over-the-counter ("OTC") module 180 or OTC application, which may access and/or be in communication with one or more suitable data storage devices and/or databases 182. The OTC module 180 may receive information associated with healthcare claim transactions and/or responses to healthcare claim transactions, and the OTC module 180 may determine whether a healthcare claim transaction was rejected or denied as a result of being directed to an OTC product that is not covered by a claims processor or payor. In the event that a healthcare claim transaction was denied as being directed to an uncovered OTC product, the OTC module 180 may facilitate a conversion of a denied response for the healthcare claim transaction to an approved response. Additionally, the OTC module 180 may determine a price for the OTC product and, as desired, various discount offers and/or available funding applicable to the OTC product. In this regard, the OTC module 180 may facilitate successful sales transactions for OTC products that are not covered by claims processors, thereby increasing revenue for healthcare providers.

Generally, network devices and systems, including one or more of the healthcare provider computer(s) 104, service provider computer(s) 106, and claims processor computer(s) 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, and claims processor computer 108 may be in communication with each other via one or more networks, such as network 110, which as described below can include one or more separate or shared private and public networks, including the Internet or a publicly switched telephone network. Each of these components—the healthcare provider computer 104, the service provider computer 106, the claims processor computer 108, and the network 110—will now be discussed in further detail.

The healthcare provider computer 104 may be associated with a healthcare provider, for example, a pharmacy, physician's office, hospital, etc. In certain embodiments, the healthcare provider may be associated with a group of healthcare providers, such as a pharmacy chain. The healthcare provider computer 104 may be any suitable processor-driven device that facilitates the processing of healthcare requests made by patients or consumers and the communication of information associated with healthcare claim transactions to the service provider computer 106, such as a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. In certain embodiments, the healthcare provider computer 104 may be a suitable point of sale device associated with a healthcare provider. The execution of the computer-implemented instructions by the healthcare provider computer 104 may form a special purpose computer or other particular machine operable to facilitate the processing of healthcare requests made by patients and the communication of information associated with healthcare claim transactions to a service provider computer 106. Additionally, in certain embodiments of the invention, the operations and/or control of the healthcare provider computer 104 may be distributed among several processing components.

In addition to having one or more processors 124, the healthcare provider computer 104 may include one or more memory devices 126, one or more input/output ("I/O") interface(s) 128, and/or one or more network interface(s) 130. The memory devices 126 may be any suitable memory devices, for example, caches, read-only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138. The data files 132 may include any suitable data that facilitates the receipt and/or processing of healthcare requests by the healthcare provider computer 104, the generation and/or processing of healthcare claim transactions that are communicated to the service provider computer 106, and/or the receipt and/or processing of responses to healthcare claim transactions and/or messages associated with healthcare claim transactions. For example, the data files 132 may include, but are not limited to, healthcare information associated with one or more patients, information associated with the service provider computer 106, information associated with one or more claims processors, and/or information associated with, one or more healthcare claim transactions. The operating system ("OS") 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user 120, such as a pharmacist or other pharmacy employee, may utilize the client module 138 in preparing and providing a prescription claim request (or other claim request) to the service provider computer 106 for delivery to the appropriate claims processor computer 108 for adjudication or other coverage/benefits determination. The healthcare provider computer 104 may also utilize the client module 138 to retrieve or otherwise receive data, messages, or responses from the service provider computer 106 and/or other components of the system 100.

In operation, the healthcare provider computer 104 may receive information associated with a healthcare request for a patient. As one example, the healthcare provider computer 104 may receive a healthcare request for a patient at a point of sale, such as in a pharmacy during a prescription fulfillment or at a physician's office during the provision of a healthcare service. As another example, the healthcare provider computer 104 may electronically receive a healthcare request from a patient computer or other patient device. The healthcare provider computer 104 may generate a healthcare claim transaction for the request, and information associated with the healthcare claim transaction may be communicated to the service provider computer 106.

The one or more I/O interfaces 128 may facilitate communication between the healthcare provider computer 104 and one or more input/output devices, for example, one or more user interface devices, such as a display, keypad, control panel, touch screen display, remote control, microphone, etc., that facilitate user interaction with the healthcare provider computer 104. For example, the one or more I/O interfaces 128 may facilitate entry of information associated with a healthcare transaction or healthcare claim request by an employee 120 of a healthcare provider, such as a pharmacy employee. The one or more network interfaces 130 may facilitate connection of the healthcare provider computer 104 to one or more suitable networks, for example, the network 110 illustrated in FIG. 1. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device configured for receiving, processing, and fulfilling requests from the healthcare provider computer 104 and/or claims processor computer 108 relating to prescription, pharmacy, benefits, and/or healthcare transactions and/or other activities. In certain embodiments, the service provider computer 106 may be a switch/router that routes healthcare claim transactions and/or other healthcare requests. For example, the service provider computer 106 may route billing requests and/or prescription claim requests communicated from the healthcare provider computer 104 to a claims processor computer 108, such as a pharmacy benefits manager ("PBM"), an insurer, a Medicare payor, another government payor, or a claims clearinghouse. In certain embodiments, the service provider computer 106 may include a suitable host server, host module, or other software that facilitates the receipt of a healthcare claim transaction from a healthcare provider computer 104 and/or the routing of the received healthcare claim transaction to a claims processor computer 108. Any number of healthcare provider computers and/or claims processor computers may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine operable to facilitate receiving, routing, and/or processing of healthcare claim transactions. The one or more processors that control the operations of the service provider computer 106 may be incorporated into the service provider computer 106 and/or in communication with the service provider computer 106 via one or more suitable networks. In certain embodiments of the invention, the operations and/or control of the service provider computer 106 may be distributed among several processing components.

Similar to the healthcare provider computer 104, the service provider computer 106 may include one or more processors 140, one or more memory devices 142, one or more input/output ("I/O") interface(s) 144, and/or one or more network interface(s) 146. The one or more memory devices 142 may be any suitable memory devices, for example, caches, read-only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a pre- and post-edit ("PPE") module 156, and a database management system ("DBMS") 152 to facilitate management of data files 148 and other data stored in the memory devices 142 and/or one or more databases 182. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The PPE module 156 may be operable to perform one or more pre-edits on a received healthcare claim transaction prior to routing or otherwise communicating the received healthcare claim transaction to a suitable claims processor computer 108. Additionally, the PPE module 156 may be operable to perform one or more post-edits on an adjudicated reply or response that is received from a claims processor computer 108 for a healthcare claim transaction prior to routing the adjudicated reply to the healthcare provider computer 104. A wide variety of different pre-edits and/or post-edits may be performed as desired in various embodiments of the invention. In certain embodiments, the OTC module 180 may be incorporated into the PPE module 156 and/or in communication with the PPE module 156. For example, in certain embodiments, the OTC module 180 may be implemented as a suitable post-edit.

According to an embodiment of the invention, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or a claims processor computer 108. The host module 154 may receive, process, and respond to requests from the client module 138 of the healthcare provider computer 104, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from example embodiments of the invention.

An OTC module 180 or OTC application may also be operative with the service provider computer 106. The OTC module 180 may include computer-executable instructions for processing adjudicated replies or responses to healthcare claim transactions in order to determine whether a denial or rejection for a healthcare claim transaction associated with one or more OTC products should be converted to an approval. In other words, the OTC module 180 may determine whether a rejection or denial of a healthcare claim transaction should be converted to an approval based upon a classification of one or more products associated with the healthcare claim transaction. In the event that OTC products are associated with a rejected healthcare claim transaction, the OTC module 180 may convert a denial to an approval. Additionally, the OTC module 180 may determine a price, such as a retail price, for the one or more OTC products. In this regard, situations in which a customer fails to complete a transaction for an OTC product may be reduced. For example, situations in which a customer walks away because a healthcare claim transaction was rejected may be reduced and/or avoided as a result of an approved claim response being returned to the healthcare provider. In this regard, additional revenue may be obtained by the healthcare provider.

In operation, the OTC module 180 may receive information associated with a rejected healthcare claim transaction and/or an adjudicated reply (e.g., a denial response) for the healthcare claim transaction. The OTC module 180 may determine whether the healthcare claim transaction was rejected because it included a claim for an OTC product. In other words, the OTC module 180 may determine whether a payor rejected the healthcare claim transaction because it was directed to one or more OTC products that are not covered by a benefits plan for a patient. A wide variety of suitable techniques and/or a combination of techniques may be utilized as desired to determine whether the claim was rejected because it was directed to an OTC product. For example, one or more messages, rejection codes, and/or rejection reasons included in the adjudicated reply may be identified and compared to pre-stored messages and/or rejection codes associated with rejections for uncovered OTC products. Examples of suitable messages and/or rejection codes that may be identified include, but are not limited to, a message indicating that OTC products are not covered (e.g., a message including the text strings "OTC" and "NOT COVERED"), a rejection code associated with a missing or invalid product identifier, and/or a rejection code indicating that a product identifier is not covered. As another example of determining whether a claim was rejected as being directed to an uncovered OTC product, one or more drugs or products associated with the healthcare claim transaction may be identified, and a determination may be made as to whether the identified drugs or products are classified at OTC products. For example, the OTC module 180 may identify products by suitable identifiers, such as National Drug Code ("NDC") identifiers or Universal Product Code ("UPC") identifiers, and the OTC module 180 may determine whether the identifiers match one or more stored identifiers associated with OTC products. Alternatively, a product identifier may be utilized to identify or determine a classification for the product, and a determination may be made as to whether the product is an OTC product.

Based upon a determination that the healthcare claim transaction was rejected as being directed to an uncovered OTC product, the OTC module 180 may facilitate a conversion of a denied or rejected response for the claim transaction to an approved response. In other words, a status of the response may be changed to an "approved" or "paid" status. Additionally, the OTC module 180 may identify or determine a price for the OTC product. A wide variety of suitable methods and/or techniques may be utilized to determine a price for the OTC product. For example, the OTC module 180 may obtain pricing parameters and/or pricing information from the one or more databases 182 and/or from any number of external data sources or other components of the system 100 (e.g., the healthcare provider computer 104, the healthcare provider back office computer 195, a product manufacturer, etc.). A wide variety of pricing parameters and/or pricing information may be utilized as desired in various embodiments of the invention, such as retail pricing information, cost basis information, per unit price information for the OTC product, a formula for calculating a price for the OTC product, pricing preferences and/or formulas for a particular healthcare provider or group of healthcare providers (e.g., a pharmacy chain, etc.), and/or other pricing information. Based at least in part upon the obtained information, the OTC module 180 may calculate a price for the OTC product. For example, the obtained information may include a pricing formula that may be utilized in conjunction with a product quantity (e.g., a product quantity included in the healthcare claim transaction) to calculate a price for the OTC product. As one example, a pricing formula and/or pricing parameters may be utilized to determine a per unit price for the product, and the per unit price may be multiplied by a product quantity to calculate a price for the product.

In certain embodiments, the OTC module 180 may identify one or more discounts that may be applied to the OTC product. For example, coupons and/or discounts offered by the healthcare provider, a manufacturer of the product, and/or another entity may be identified. Once identified, the OTC module 180 may determine whether the discounts are eligible for application to the OTC product. For example, the OTC module 180 may determine whether one or more threshold conditions for applying the various discounts (e.g., a minimum purchase condition, a geographical condition, a bundled products condition, etc.) have been met. Based upon the results of the determinations, the OTC module 180 may apply one or more of the discounts in order to reduce or modify the price of the OTC product.

As desired in certain embodiments, the OTC module 180 may identify one or more sources of funding that may be utilized to pay for a portion or all of the OTC product. A wide variety of different sources of funding may be identified as desired, such as funding offered by a pharmaceutical manufacturer, funding offered by a healthcare provider, or funding offered by another entity. As desired, the OTC module 180 may analyze a wide variety of available funding information and/or communicate a wide variety of funding requests to various entities (e.g., potential funding sources) in order to determine whether funding is available. If the OTC module 180 determines that one or more sources of funding are available, then the OTC module 180 may reduce or modify the price of the OTC product to reflect the available funding. The OTC module 180 may then coordinate the receipt and/or distribution of other funding to assist in paying for the OTC product.

Following the determination of a price for the OTC product, the OTC module 180 may modify the converted response to the healthcare claim transaction to reflect the determined price. For example, one or more pricing fields associated with the converted response may be modified. As one example, a "total amount paid" field may be modified to reflect that no money has been paid (or to reflect amounts paid by alternative funding sources), a "patient pay" field may be modified to reflect the computed price, an "ingredient cost" field may be modified to reflect a cost basis that has been utilized, and a "fee" field may be modified to be equal to the total fees for the product. In this regard, financial information for the healthcare claim transaction may be balanced.

Once a response has been converted and/or modified, the OTC module 180 may direct the routing or communication of the converted response to the healthcare provider computer 104. For example, the OTC module 180 may direct the service provider computer 106 to route the converted response to the healthcare provider computer 104. Additionally, in certain embodiments, the OTC module 180 may append one or more messages to the converted response. For example, a message indicating that a rejected response has been converted and/or a message indicating that the original claim was rejected as a result of being directed to an uncovered OTC product may be generated and appended to the converted response. As an alternative to appending one or more messages to a converted response or converted adjudicated reply, the OTC module 180 may communicate or direct the communication of a generated message to the healthcare provider computer 104 and/or to other devices associated with the healthcare provider, such as a fax machine, a printer, another computer associated with the healthcare provider, and/or a mobile device. A wide variety of suitable communication techniques may be utilized as desired to communicate a message to a device associated with the healthcare provider, such as email, short message service ("SMS") messaging, network-packet communications, etc.

In certain embodiments, the OTC module 180 may identify one or more rules or parameters that are applicable for processing an adjudicated reply to a healthcare claim transaction. For example, the OTC module 180 may identify one or more applicable rules or parameters based upon an identity of the healthcare provider that submitted the claim transaction or a group of healthcare providers (e.g., a pharmacy chain) in which the healthcare provider is included. The identified rules may include rules associated with various processing steps to be performed on an adjudicated reply by the OTC module 180. For example, the identified rules may include parameters for calculating a price and/or preferences for communicating one or more messages to the healthcare provider.

Additionally, as desired, the OTC module 180 may store or direct the storage of information associated with the healthcare claim transaction in the databases or data storage devices 182. For example, the OTC module 180 may store the healthcare claim transaction, information extracted from the healthcare claim transaction, the adjudicated reply, information extracted from the adjudicated reply, information associated with a conversion, price information, information associated with one or more generated messages, and/or information associated with the rules applied by the OTC module 180. In certain embodiments, the stored information may be utilized for billing and/or reporting purposes.

The data storage devices 182 may be operable to store information associated with various rules and/or parameters that may be utilized by the OTC module 180 to process adjudicated replies and/or healthcare claim transactions. For example, rules may be received from one or more other components of the system 100, such as the healthcare provider computer 104, the healthcare provider back office computer 195, and/or the claims processor computer 108, and at least a portion of the received rules may be stored. Additionally, the data storage devices 182 may be operable to store information associated with healthcare claim transactions, adjudicated replies, and/or processing performed by the OTC module 180. In certain embodiments, the data storage devices 182 may additionally store billing information associated with the healthcare claim transactions and/or reports associated with the healthcare claim transactions and/or processing of the healthcare claim transactions and/or adjudicated replies. The data storage devices 182 may be accessible by the OTC module 180 and/or the service provider computer 106.

In certain embodiments, the OTC module 180 and/or the service provider computer 106 may be operable to generate one or more reports associated with processed healthcare claim transactions and/or adjudicated replies. A wide variety of different types of reports may be generated as desired in various embodiments of the invention. Additionally, a wide variety of different information may be incorporated into the generated reports, including but not limited to, a number of times the OTC module 180 was invoked for a healthcare provider or group of healthcare providers (e.g., a pharmacy chain), information associated with the results of various processing performed by the OTC module 180, date information and/or date range information associated with the processed healthcare claim transactions and/or adjudicated replies, financial information associated with the healthcare claim transactions, and/or billing information associated with the invocation of the OTC module 180 for the healthcare claim transactions. Reports may be sorted or formatted utilizing a wide variety of different criteria, parameters, and/or techniques. Additionally, the OTC module 180 may communicate or direct the communication of generated reports to one or more other components of the system, for example, the healthcare provider computer 104 and/or a healthcare provider back office computer 195 associated with a group of healthcare providers.

A wide variety of different techniques and/or software programs may be utilized to format a generated report. For example, a report may be formatted as a comma-separated-value ("csv") file, as a spreadsheet file, as a word processor file, as a text file, etc. Additionally, a wide variety of different communication techniques may be utilized to communicate a report to the recipient, including but not limited to, email, short message service ("SMS") messaging, other electronic communications, snail mail, etc. A report may be pushed to a recipient by the OTC module 180 or other reporting module, or, alternatively pulled from the OTC module 180 by a recipient submitting a request for one or more reports. Additionally, in certain embodiments, a report may be made available for download from an appropriate web site or server, such as a web site hosted by the service provider computer 106.

The operations of the OTC module 180 and/or the data storage devices 182 are described in greater detail below with reference to FIGS. 3-4.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc., that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

With continued reference to FIG. 1, the claims processor computer 108 may be any suitable processor-driven device that facilitates receiving, processing, and/or fulfilling healthcare claim transactions and/or healthcare claim requests received from the service provider computer 106. For example, the claims processor computer 108 may be a processor-driven device associated with a pharmacy benefits manager ("PBM"), an insurer, a Medicare payor, another government payor, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare claim transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed among several processing components.

Similar to other components of the system 100, the claims processor computer 108 may include one or more processors 158, one or more memory devices 160, one or more input/output ("I/O") interface(s) 162, and/or one or more network interface(s) 164. The one or more memory devices 160 may be any suitable memory devices, for example, caches, read-only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient benefits eligibility and/or insurance information, other information associated with a patient, information associated with a healthcare provider, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information utilized by the claims processor computer 108 in various embodiments of the invention. The host module 172 may initiate, receive, process, and/or respond to requests, such as healthcare claim transactions or claim requests, from the host module 154 of the service provider computer 106. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, the network 110 illustrated in FIG. 1. In this regard, the claims processor computer 108 may receive healthcare claim transactions and/or other communications from the service provider computer 106, and the claims processor computer 108 may communicate information associated with processing claim transactions to the service provider.

The healthcare provider back office computer 195 may be one or more computers associated with a group of healthcare providers, such as a chain of pharmacies. The healthcare provider back office computer 195 may include components similar to other devices included in the system 100, such as the healthcare provider computer 104. For example, the healthcare provider back office computer 195 may be a processor-driven device that includes at least one memory, at least one processor, one or more I/O interfaces and/or one or more network interfaces. The healthcare provider back office computer 195 may further include software and/or computer-executable instructions that may be executed by the at least one processor to receive reports and/or billing information associated with the processing of healthcare claim transactions by the OTC module 180. Additionally, as desired, the healthcare provider back office computer 195 may be operable or configured to provide various rules, parameters, preferences, and/or pricing information associated with processing healthcare claim transactions and/or adjudicated replies to the service provider computer 106 and/or the OTC module 180.

The network 110 may include any telecommunication and/or data network, whether public, private, or a combination thereof, including a local area network, a wide area network, an intranet, the Internet, intermediate handheld data transfer devices, and/or any combination thereof and may be wired and/or wireless. The network 110 may also allow for real-time, off-line, and/or batch transactions to be transmitted between or among the healthcare provider computer 104, the service provider computer 106, and the claims processor computer 108. Due to network connectivity, various methodologies as described herein may be practiced in the context of distributed computing environments. Although the service provider computer 106 is shown for simplicity as being in communication with the healthcare provider computer 104 or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 106 may form the basis of a network 110 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the OTC module 180, may be implemented as part of the claims processor computer 108 or as part of the healthcare provider computer 104. Accordingly, embodiments of the invention should not be construed as being limited to any particular operating environment, system architecture, or device configuration.

Operational Overview

Figure 2A:
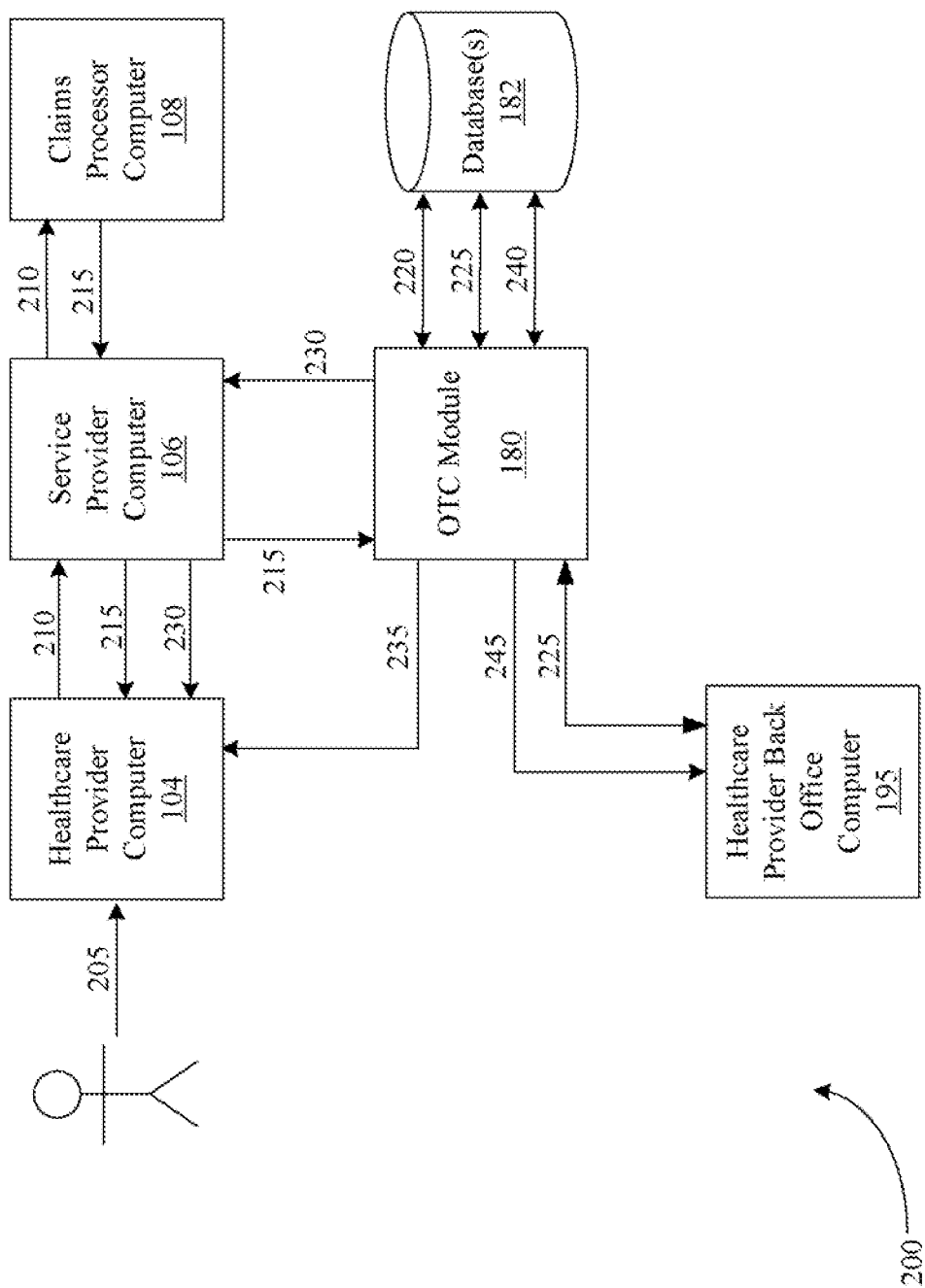

FIG. 2A is a block diagram of one example data flow 200 for processing claim transactions for OTC products that are processed through a service provider, such as the service provider computer 106 illustrated in FIG. 1. With reference to FIG. 2A, a healthcare provider computer, such as the healthcare provider computer 104 illustrated in FIG. 1, may receive a healthcare request 205 from a patient, such as a request associated with a prescription. The healthcare request 205 may be received in-person or electronically as desired in various embodiments of the invention. For example, a patient may request a product at a pharmacy or physician's office. As another example, a patient may communicate a healthcare request 205 to a healthcare provider computer 104 via one or more suitable network connections. For example, a purchase request for a product may be communicated to a healthcare provider computer 104 from a customer computer via a web portal hosted by the healthcare provider computer 104.

The healthcare provider computer 104 may receive and process the request 205 to generate a healthcare claim transaction 210, such as a healthcare claim request or a prescription claim request, and the healthcare claim transaction 210 may be communicated by the healthcare provider computer 104 to the service provider computer 106. According to an aspect of the invention, the healthcare claim transaction 210 may be associated with an OTC product. According to an example embodiment of the invention, the healthcare claim transaction 210 may be in accordance with a version of a National Council for Prescription Drug Programs ("NCPDP") Telecommunication Standard, although other standards may be utilized as well. As desired, the healthcare claim transaction 210 may include a Banking Identification Number ("BIN") and/or a Processor Control Number ("PCN") for identifying a particular claims processor computer or payor, such as the claims processor computer 108 illustrated in FIG. 1, as a destination for the healthcare claim transaction 210. In addition, the healthcare claim transaction 210 may also include information relating to the patient, payor, prescriber, healthcare provider, and/or the prescribed or administered drug, product, or service. As an example, the healthcare claim transaction 210 received by the service provider computer 106 may include one or more of the following information:

Payor ID/Routing Information
    BIN Number (i.e. Banking Identification Number) and/or Processor Control Number (PCN) that designates a destination of the healthcare claim transaction 210
    Patient Information
    Name (e.g., Patient Last Name, Patient First Name, etc.)
    Date of Birth of Patient
    Age of Patient
    Gender
    Patient Address (e.g., Street Address, Zip Code, etc.)
    Patient Contact Information (e.g., Patient Telephone Number, email address, etc.)
    Patient ID or other identifier
    Insurance/Coverage Information
    Cardholder Name (e.g., Cardholder First Name, Cardholder Last Name)
    Cardholder ID and/or other identifier (e.g., person code)
    Group ID and/or Group Information
    State Payor Information
    Prescriber Information
    Primary Care Provider ID or other identifier (e.g., National Provider Identifier (NPI) code)
    Primary Care Provider Name (e.g., Last Name, First Name)
    Prescriber ID or other identifier (e.g., NPI code, DEA number)
    Prescriber Name (e.g., Last Name, First Name)
    Prescriber Contact Information (e.g., Telephone Number)
    Pharmacy or other Healthcare Provider Information (e.g., store name, chain identifier, etc.)
    Pharmacy or other Healthcare Provider ID (e.g., NPI code)
    Claim Information
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)
    One or more NCPDP Message Fields
    One or more Drug Utilization Review (DUR) Codes
    Date of Service.

With continued reference to FIG. 2A, the service provider computer 106 may receive the healthcare claim transaction 210 from the healthcare provider computer 104, and the service provider computer 106 may process the healthcare claim transaction 210. As desired, the service provider computer 106 may perform one or more pre-edits on the healthcare claim transaction 210. The pre-edits may verify, add, and/or edit information included in the healthcare claim transaction 210 prior to the healthcare claim transaction 210 being communicated to an appropriate claims processor computer 108. Following any pre-edits, the healthcare claim transaction 210 and/or a copy thereof may be routed or otherwise communicated by the service provider computer 106 to an appropriate claims processor computer 108 associated with a designated payor for adjudication. According to an example embodiment, the service provider computer 106 may utilize at least a portion of the information included in the healthcare claim transaction 210, such as a BIN/PCN, to determine the appropriate claims processor computer 108 to route the healthcare claim transaction 210 to. The service provider computer 106 may also include a routing table, perhaps stored in memory, for determining which claims processor computer 108 to route the healthcare claim transaction 210 to.

The claims processor computer 108 may receive and adjudicate or otherwise process the healthcare claim transaction 210. For example, the claims processor computer 108 may determine benefits coverage for the healthcare claim transaction 210 according to an adjudication process associated with eligibility, pricing, and/or utilization review. The claims processor computer 108 may transmit an adjudicated reply 215 or response for the healthcare claim transaction 210 to the service provider computer 106. The service provider computer 106 may receive the adjudicated reply 215 from the claims processor computer 108. As desired, the service provider computer 106 may perform any number of post-edits on the adjudicated reply 215. In certain embodiments, a determination may be made as to whether an OTC reprice edit or service is enabled for the healthcare claim transaction 210 and/or the adjudicated reply 215. For example, a determination may be made as to whether a healthcare, provider or group of healthcare providers associated with the claim transaction 210 has enabled or activated an OTC reprice edit for use in processing adjudicated replies that are routed or otherwise communicated through the service provider computer 106. As desired, one or more threshold conditions for invoking an OTC reprice edit may be evaluated in order to determine whether the edit should be invoked. For example, a determination may be made as to whether the adjudicated reply 215 indicates that the healthcare claim transaction 210 was rejected. As another example, a determination may be made as to whether an OTC product is associated with the healthcare claim transaction 210.

If an OTC reprice edit is enabled for processing the adjudicated reply 215 and/or the healthcare claim transaction 210, then the adjudicated reply 215, a copy of the reply 215, and/or information included in the reply 215 may be communicated to a suitable OTC module, such as the OTC module 180 shown in FIG. 1, for processing. As desired, information included in and/or associated with the healthcare claim transaction 210 may also be communicated to the OTC module 180. The OTC module 180 may receive the adjudicated reply 215 (and optionally the healthcare claim transaction 210), and the OTC module 180 may determine whether the healthcare claim transaction 210 was rejected because it was directed to an OTC product for which benefits coverage is not available. During the processing of the adjudicated reply 215, the OTC module 180 may access a wide variety of processing rules and/or parameters 220 from one or more suitable databases, such as the databases 182 illustrated in FIG. 1. For example, processing rules and/or parameters associated with a healthcare provider or group of healthcare providers may be accessed. Examples of suitable processing rules and/or parameters 220 include, but are not limited to, rules for identifying eligible replies for conversion (e.g., rules for determining eligible rejection reasons for conversion), reporting preferences, and/or messaging preferences.

A wide variety of suitable techniques may be utilized as desired to determine whether the healthcare claim transaction 210 was rejected because it was directed to an uncovered OTC product. For example, one or more rejection codes included in the adjudicated reply 215 may be identified, and the rejection code(s) may be analyzed and/or evaluated to determine whether the healthcare claim transaction 210 was rejected because it was directed to an uncovered OTC product. As another example, the OTC module 180 may parse and/or analyze the adjudicated reply 215 in order to determine whether any included messages indicate that the healthcare claim transaction 210 was rejected as being directed to an uncovered OTC product. For example, the OTC module 180 may search for messages included the text strings "OTC" and "NOT COVERED." A wide variety of different text strings and/or messages may be identified and/or evaluated as desired in various embodiments of the invention. If it is determined that the healthcare claim transaction 210 was not rejected because it was directed to an uncovered OTC product, then the OTC module 180 may direct the service provider computer 106 to route or communicate the adjudicated reply 215 to the healthcare provider computer 104. If, however, it is determined that the healthcare claim transaction 210 was rejected because it was directed to an uncovered OTC product, then the OTC module 180 may convert the rejected adjudicated reply 215 into an approved reply 230, also referred to as a converted adjudicated reply 230 or converted reply 230.

Additionally, during the processing of the adjudicated reply 215, the OTC module 180 may calculate or determine a price for the OTC product. In doing so, the OTC module 180 may obtain pricing information 225, such as pricing formulas, retail price information, and/or other pricing information. For example, a product identifier of the OTC product, such as a National Drug Code ("NDC") identifier, a Universal Product Code ("UPC") identifier, and/or a product name, may be identified and utilized to obtain pricing information. As desired, the pricing information 225 may be obtained from a wide variety of different sources, such as the databases 182 and/or any number of external sources, such as the healthcare provider back office computer 195 illustrated in FIG. 1. The pricing information may be utilized by the OTC module 180 in a calculation or determination of a price for the OTC product. Additionally, information included in the healthcare claim transaction 210 and/or the adjudicated reply 215, such as quantity information for the OTC product, may be utilized to calculate a price for the OTC product. The calculated-price may then be utilized to modify pricing information for the converted adjudicated reply 230. In certain embodiments, the OTC module 180 may identify discount offers (e.g., coupons, promotional discounts, etc.) and/or alternative sources of funding that are available for the OTC product. The OTC module 180 may apply discounts and/or available funding in order to reduce and/or modify a calculated price for the OTC product.

Once the converted adjudicated reply 230 has been generated and/or modified, the OTC module 180 may provide the converted reply 230 or a copy thereof to the service provider computer 106, and the service provider computer 106 may route or communicate the converted reply 230 to the healthcare provider computer 104. In this regard, an approved response for the initially rejected healthcare claim transaction 210 may be received by the healthcare provider computer.

As desired, the OTC module 180 may append any number of messages, indications, and/or other information to the converted reply 230. Additionally or alternatively, the OTC module 180 may generate one or more messages 235 that may be separately communicated to the healthcare provider computer 104 by the OTC module 180 or at the direction of the OTC module 180. For example, the OTC module 180 may communicate one or more generated messages 235 to the service provider computer 106, and the service provider computer 106 may communicate the messages 235 to the healthcare provider computer 104. As another example, the OTC module 180 may directly communicate the messages 235 to the healthcare provider computer 104 and/or other devices (e.g., a printer, a fax machine, etc.) associated with the healthcare provider. A wide variety of messages may be generated as desired in various embodiments of the invention. For example, a message including an indication that the healthcare claim transaction 210 was initially rejected and the denial response 215 has been converted to an approved response 230 may be generated. As another example, a message may be generated that includes information associated with the calculation of a price.

According to an aspect of the invention, the OTC module 180 may store information 240 associated with the processed adjudicated reply 215, converted reply 230, and/or healthcare claim transaction 210 for reporting and/or billing purposes. A wide variety of information 240 may be stored as desired in various embodiments of the invention, for example, a copy of the healthcare claim transaction 210, information extracted from the healthcare claim transaction 210, a copy of the adjudicated reply 215, information extracted from the adjudicated reply 215, information associated with the processing of the OTC module 180, information associated with a converted reply 230, financial information associated with the conversion, pricing information, discount information, alternative funding information, etc. In certain embodiments, information associated with the invocation of the OTC module 180 may be communicated to an appropriate billing system associated with the service provider computer 106 in order to facilitate billing customers, such as healthcare providers, for the services provided by the OTC module 180. Alternatively, the OTC module 180 may alter a billing code or other field of the healthcare claim transaction 210 to a value indicating that the healthcare claim transaction 210 has been evaluated or processed by the OTC module 180. The altered billing code may be recognized during subsequent or further processing of the healthcare claim transaction 210, such as further processing by the service provider computer 106, in order to facilitate billing.

According to another aspect of the invention, the OTC module 180 or a reporting system associated with the OTC module 180 and/or service provider computer 106 may utilize at least a portion of stored information 240 to generate one or more reports 245 that include information associated with the processing of the healthcare claim transaction 210 and/or the adjudicated reply 215. The generation of reports 245 is discussed in greater detail above with respect to FIG. 1. As desired, generated reports 245 may be communicated to customers of the service provider or to customer systems and/or devices, for example, the healthcare provider computer 104 and/or to the healthcare provider back office computer 195. A wide variety of suitable communications techniques, for example, electronic mail, short message service ("SMS") messaging, other electronic communications, snail mail, etc., may be utilized as desired to communicate generated reports 245 to one or more recipients.

It will be appreciated that variations of the data flow 200 illustrated in FIG. 2A may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and the claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the OTC module 180. For example, a first service provider may communicate claims, adjudicated replies, and/or other information to a second service provider for processing.

As described herein, healthcare transactions and/or adjudicated replies may be examined as they are routed to or through a service provider computer 106. In this regard, an OTC reprice service may be provided in real-time or near real-time as the healthcare transactions and/or adjudicated replies are routed to or through the service provider computer 106. FIG. 3 is a flow diagram of an example method 300 for processing a healthcare claim transaction for an OTC product, according to an illustrative embodiment of the invention. The method 300 may be performed by a suitable service provider computer and/or an associated OTC module, such as the service provider computer 106 and the OTC module 180 illustrated in FIG. 1. The method 300 may begin at block 305.

At block 305, a healthcare claim transaction may be received from a healthcare provider computer, such as the healthcare provider computer 104 shown in FIG. 1. One or more pre-edits and/or evaluations may be performed on the received healthcare claim transaction as desired in various embodiments of the invention. For example, one or more pre-edits may be performed by a PPE module associated with the service provider computer 106, such as the PPE module 156 shown in FIG. 1. At block 310, the healthcare claim transaction may then be routed or otherwise communicated to an appropriate claims processor computer for adjudication, such as the claims processor computer 108 illustrated in FIG. 1.

The claims processor computer 108 may adjudicate the healthcare claim transaction and determine a wide variety of benefits and/or coverage information. For example, the claims processor computer 108 may identify one or more products associated with the healthcare claim transaction and determine whether the one or more products are covered by a patient benefit plan. Following the adjudication, the claims processor computer 108 may communicate an adjudicated reply or response to the service provider computer 106, and the response may be received at block 315. A wide variety of information may be included in the response in various embodiments of the invention, such as an indication of whether the healthcare claim transaction has been approved or rejected, one or more rejection codes in the event that the transaction has been rejected, and/or one or more message fields.

Once received by the service provider computer 106, a wide variety of post-edits and/or evaluations may be performed on the received response as desired in various embodiments of the invention. For example, one or more post-edits may be performed by the PPE module 156. At block 320, a determination may be made as to whether the response indicates that the underlying healthcare claim transaction has been rejected. For example, a received adjudicated reply may be analyzed and/or evaluated in order to determine whether the healthcare claim transaction has been rejected. If it is determined at block 320 that the healthcare claim transaction has not been rejected or that the healthcare claim transaction has been approved, then operations may continue at block 325. At block 325, the received adjudicated reply or response may be routed or otherwise communicated to the healthcare provider computer 104. Operations may then end following block 325.

If, however, it is determined at block 320 that the healthcare claim transaction has been rejected, then operations may continue at block 330. At block 330, a determination may be made as to whether an OTC reprice edit has been enabled. For example, a determination may be made as to whether an OTC reprice edit has been enabled and/or activated for a healthcare provider that submitted the healthcare claim transaction or for a group of healthcare providers (e.g., a pharmacy chain) to which the healthcare provider belongs. If it is determined at block 325 that an OTC reprice edit has not been enabled, then operations may continue at block 325 described above, and the received adjudicated reply may be routed or otherwise communicated to the healthcare provider computer 104. If, however, it is determined at block 330 that an OTC reprice edit has been enabled, then operations may continue at block 335.

At block 335, the received response or adjudicated reply and/or the underlying healthcare claim transaction may be processed utilizing the OTC reprice edit. For example, the response may be processed by the OTC module 180 or OTC application. The OTC module 180 may determine whether the healthcare claim transaction was rejected as being directed to an uncovered OTC product. If it is determined that the transaction was rejected as being directed to an uncovered OTC product, then the OTC module 180 may convert the denial response or rejection response into an approved response. Additionally, in certain embodiments, the OTC module 180 may generate a wide variety of suitable messages associated with the processing performed, such as messages associated with a conversion and/or determination of pricing information. One example of the operations that may be performed by the OTC module 180 in order to evaluate or process the response and/or healthcare claim transaction is described in greater detail below with reference to FIG. 4.

At block 340, one or more messages and/or a claim response (e.g., an original response or a converted response) may be routed or otherwise communicated by the service provider computer 106 to the healthcare provider computer 104 and/or other suitable devices associated with the healthcare provider (e.g., a fax machine, etc.). As desired, the communication of messages and/or claim responses may be based at least in part upon the processing performed by the OTC module 180. As set forth above, a wide variety of suitable messages may be generated by the OTC module 180 and communicated to a healthcare provider. As desired, the OTC module 180 may append information (e.g., messages, override information, instructions, etc.) to an adjudicated reply prior to the adjudicated reply being communicated to the healthcare provider. Operations may then continue at block 345.

At block 345, which may be optional in certain embodiments of the invention, information associated with the healthcare claim transaction and/or the invocation of the OTC module 180 may be stored and/or communicated for billing and/or reporting purposes. As explained in greater detail above, a wide variety of information may be stored in various embodiments of the invention. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the OTC reprice service provided by the OTC module 180. A wide variety of different types of billing information may be stored and/or communicated as desired in various embodiments of the invention, for example, an identifier associated with the invocation of the OTC module 180 or a billing code (e.g., a unique billing code) associated with the invocation of the OTC module 180. As an alternative to storing or communicating billing information, the OTC module 180 may set a billing code for the healthcare claim transaction and/or an adjudicated reply to a unique billing code associated with the provided OTC reprice service. The unique billing code may be identified or recognized during subsequent processing of the healthcare claim transaction and/or adjudicated reply by either the billing system or a component of the service provider computer 106. The identified billing code may then be utilized by the billing system in the generation of bills for customers of the service provider.

At block 350, which may be optional in certain embodiments of the invention, one or more reports may be generated utilizing at least a portion of the stored information. For example, reports may be generated by the OTC module 180, the service provider computer 106, and/or a separate reporting module. A wide variety of different information may be included in a generated report, including but not limited to, information extracted from one or more healthcare claim transactions and/or adjudicated replies, information associated with the conversion of a denial response, OTC product information, pricing information, invocation information associated with the OTC module 180, invocation rate information for the OTC module 180, financial information, billing information, etc. Additionally, generated reports may be formatted and/or sorted utilizing a wide variety of different parameters and/or criteria, such as identifiers for healthcare provider computers, identifiers for healthcare providers, identifiers for products and/or services associated with healthcare claim transactions, dates of service, etc. As desired, generated reports may be communicated to one or more recipients, such as the healthcare provider computer 104 and/or a healthcare provider back office computer, such as the back office computer 195 illustrated in FIG. 1.

The method 300 may end following either block 325 or 350.

Figure 3:
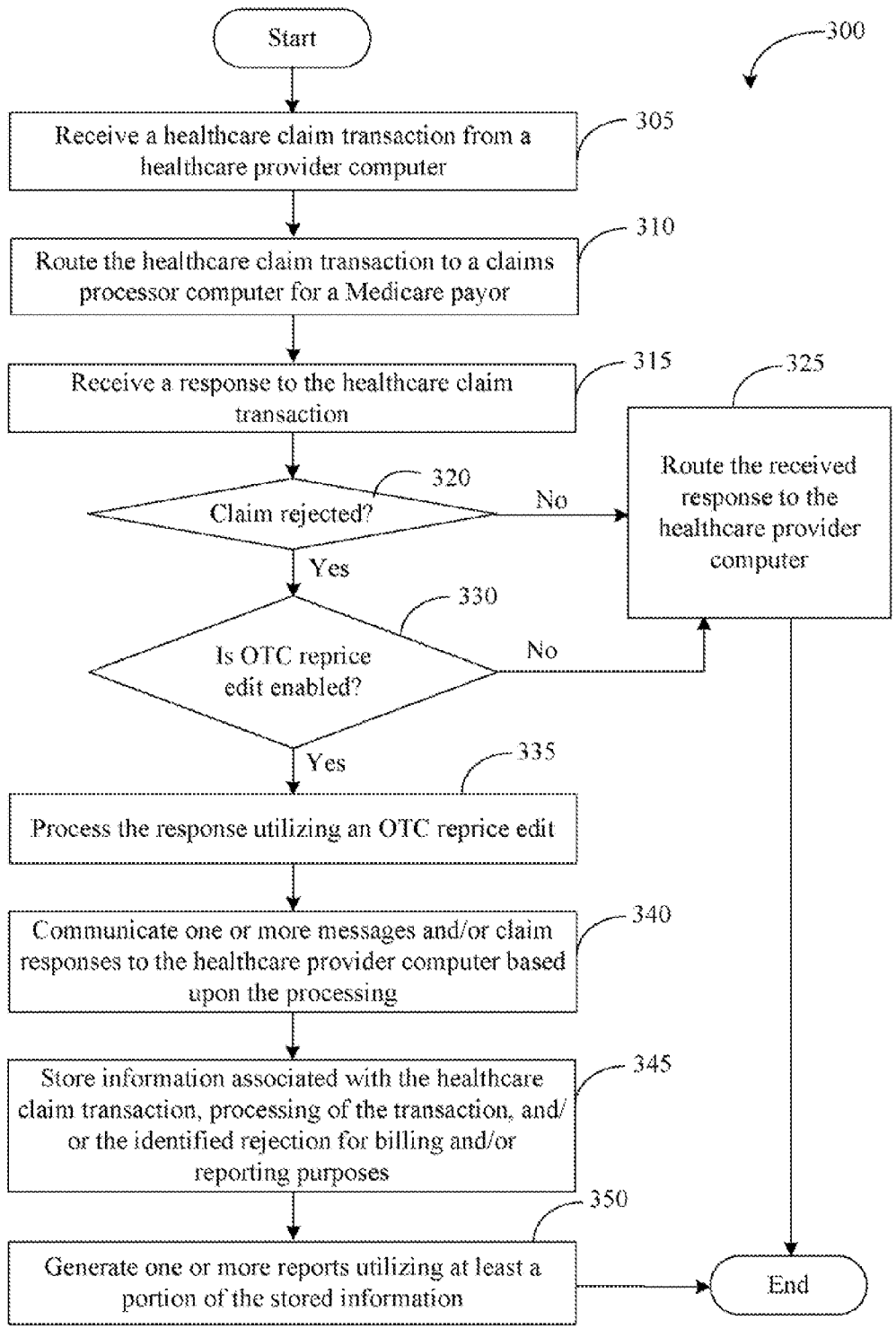
FIG. 3 is a flow diagram of an example method for processing a claim transaction for an over-the-counter product, according to an illustrative embodiment of the invention.
Figure 4:
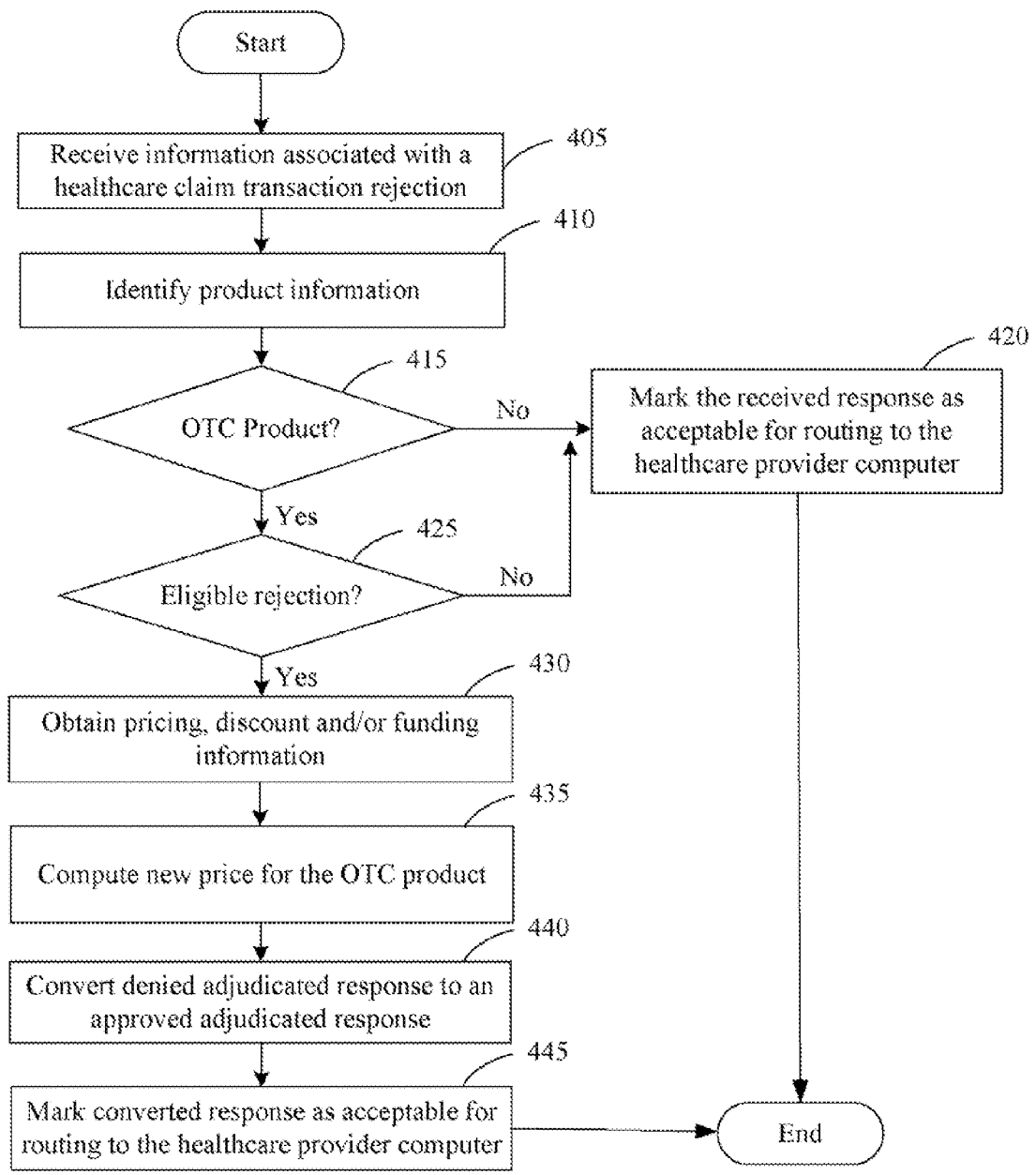
FIG. 4 is a flow diagram of an example method for processing a rejected claim transaction for an over-the-counter product, according to an illustrative embodiment of the invention.

FIG. 4 is a flow diagram of an example method 400 for processing a rejected claim transaction for an OTC product, according to an illustrative embodiment of the invention. The method 400 illustrated in FIG. 4 may be an example implementation of block 335 shown in FIG. 3. As such, the method 400 may be performed by a suitable service provider computer and/or OTC module, such as the service provider computer 106 and/or the OTC module 180 illustrated in FIG. 1. The method 400 may begin at block 405.

At block 405, information associated with a rejected healthcare claim transaction may be received, such as a copy of a received denial response, a copy of the underlying healthcare claim transaction, and/or information extracted from the response and/or the healthcare claim transaction.

At block 410, information associated with a product included in the healthcare claim transaction may be identified. A wide variety of product information may be identified as desired, such as a product name, one or more product identifiers (e.g., a NDC identifier, a UPC identifier, etc.), a product type or product classification, and/or a quantity associated with the product (e.g., a quantity dispensed). At block 415, which may be optional in certain embodiments of the invention, a determination may be made as to whether the product is an OTC product. For example, a product name and/or identifier may be compared to prestored names and/or identifiers for the OTC product. In the event that a match is found, the product may be identified as an OTC product. As another example, a product type or classification may be analyzed in order to determine whether the product is an OTC product. If it is determined at block 415 that the product is not an OTC product, then operations may continue at block 420. At block 420, the received adjudicated reply (e.g., the denial response) may be marked as an acceptable response for routing to an appropriate healthcare provider computer 104. If, however, it is determined at block 415 that the product is an OTC product, then operations may continue at block 425.

At block 425, a determination may be made as to whether the rejection or denial is eligible for conversion. In other words, a determination may be made as to whether the rejection satisfies any number of threshold conversion conditions. For example, a determination may be made as to whether the healthcare claim transaction was rejected because it includes a claim for an uncovered OTC product. As another example, a determination may be made as to whether the healthcare provider has authorized a conversion for the healthcare claim transaction based upon any number of parameters, such as product parameters, geographical parameters, etc. In certain embodiments, one or more rejection codes (e.g., NCPDP reject codes) included in the denial response may be analyzed or evaluated in order to facilitate a determination of whether the claim transaction was rejected as being directed to an uncovered OTC product. For example, a rejection code may be identified, and the rejection code may be compared to one or more predefined or pre-stored rejection codes associated with a potential OTC product rejection. In the event that a match or correspondence is found, it may be determined that the healthcare claim transaction was rejected or likely rejected because it was directed to an uncovered OTC product. Examples of suitable rejection codes that may be utilized for uncovered OTC product rejections include, but are not limited to, a missing or invalid NDC rejection or an NDC not covered rejection. In addition to or as an alternative to evaluating one or more rejection codes, one or more messages included in the adjudicated reply may be analyzed and/or evaluated in order to determine whether the healthcare claim transaction was rejected because it was directed to an uncovered OTC product. A wide variety of suitable messages and/or text strings may be identified and/or evaluated as desired. As one example, the identification of a text string stating "OTC" or "OVER THE COUNTER" and "NOT COVERED" (or similar language) may be utilized in a determination that the rejection is an uncovered OTC product rejection. If it is determined at block 425 that the denial response is not an OTC denial response eligible for conversion, then operations may continue at block 420 described above, and the received adjudicated reply may be marked as an acceptable response for routing to an appropriate healthcare provider computer 104. If, however, it is determined at block 425 that the denial response is an OTC product denial eligible for conversion, then operations may continue at block 430.

At block 430, pricing information for the OTC product may be obtained. For example, a product identifier may be utilized to access pricing information from memory and/or to request pricing information from one or more external data sources, such as a healthcare provider back office computer. A wide variety of pricing information may be obtained as desired in various embodiments of the invention, such as one or more pricing formulas, retail pricing information, usual and customary pricing information, cost basis information, etc. As desired, the pricing information may be obtained based upon any number of transaction parameters, such as a geographical location of the healthcare provider that submitted the healthcare claim transaction, an identification of and/or a group of healthcare providers (e.g., a pharmacy chain) to which the healthcare provider belongs.

Additionally, in certain embodiments, any number of discount offers and/or alternative funding sources that may be applicable for the OTC product may be identified. For example, a discount offer that is potentially available for the OTC product may be identified, and a determination may be made as to whether the discount offer may be applied to reduce or cover a price of the OTC product. As desired, a determination may be made as to whether any number of threshold conditions for applying a discount offer have been satisfied, such as eligible product conditions, concurrent purchasing conditions (e.g., a purchase of multiple products that trigger a discount), cumulative purchasing conditions (e.g., cumulative purchasing conditions for a particular transaction, cumulative purchasing over a historical time period, etc.), geographical conditions, and/or any other suitable conditions. As another example, alternative funding sources may be identified, and a determination may be made as to whether funding is available for the OTC product. For example, a determination may be made as to whether one or more entities (e.g., a product manufacturer, a healthcare provider, etc.) offer partial or complete funding for the product.

At block 435, a price for the OTC product may be computed, calculated, or determined. For example, a product formula may be utilized to calculate a price for the OTC product. In one example embodiment, product price information (e.g., retail pricing information, etc.) and product quantity information may be utilized to calculate a price for the OTC product. As desired, available discount offers and/or alternative funding information may be utilized to reduce or otherwise modify a calculated price.

At block 440, the denial response or denied adjudicated reply may be converted to an approval response or approved adjudicated reply. In doing so, a status of the adjudicated reply may be changed from "denied" or "rejected" to "approved" or "paid." Additionally, as desired, a record of the conversion may be stored for financial accounting purposes. In certain embodiments, one or more pricing fields associated with the adjudicated reply may be modified. As one example, a "total amount paid" field may be modified to reflect that no money has been paid (or to reflect amounts paid by alternative funding sources), a "patient pay" field may be modified to reflect the computed price, an "ingredient cost" field may be modified to reflect a cost basis that has been utilized, and a "fee" field may be modified to be equal to the total fees for the product. In this regard, financial information for the healthcare claim transaction may be balanced.

At block 445, the converted response may be marked as acceptable for routing or other communication to the healthcare provider computer. In this regard, an approved response may be returned to the healthcare provider, thereby increasing the likelihood that a transaction for the OTC product will be completed. Additionally, in certain embodiments, any number of messages may be generated and appended to the converted response and/or marked for separate communication to the healthcare provider. For example, a message indicating that a denial response has been converted may be generated. As another example, a message associated with the calculation of a price, the application of one or more discount offers, and/or the use of alternative funding may be generated.

The method 400 may end following either block 420 or 445.

The operations described and shown in the methods 300 and 400 of FIGS. 3-4 may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3-4 may be performed.

Accordingly, example embodiments of the invention can provide the technical effects of creating a system, method, and apparatus that converts denial responses for OTC products to approved responses. In this regard, healthcare claims that are initially rejected because they are directed to OTC products may be identified as approved claims to healthcare providers. Accordingly, increased revenue may be generated for healthcare providers, and customer or patient satisfaction may be enhanced.

Various block and/or flow diagrams of systems, methods, apparatuses, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means, for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method, comprising:
    receiving, at a service provider computer from a healthcare provider computer, a healthcare claim transaction associated with a product requested by a customer;
    communicating, by the service provider computer, the healthcare claim transaction from the service provider computer to a claims processor for adjudication;
    receiving, at the service provider computer from the claims processor, an adjudicated denied claim response for the healthcare claim transaction, wherein the adjudicated denied claim response indicates denial of any financial coverage for the healthcare claim transaction and wherein the adjudicated denied claim response is not transmitted to the healthcare provider computer;
    determining, by the service provider computer, a classification of the product requested by the customer, wherein the classification identifies the product as an over-the-counter product;
    converting, at the service provider computer, based at least in part upon the determined classification of the product, the denied claim response from the claims processor to an approved claim response, the approved claim response indicating approval of at least a portion of a price of the requested product; and
    communicating, by the service provider computer, the approved claim response from the service provider computer to the healthcare provider computer.

2. The computer-implemented method of claim 1, wherein converting the denied claim response comprises:
    determining that the healthcare claim transaction was denied based at least in part on the over-the-counter product not being covered by the claims processor; and
    converting the denied claim response at the service provider computer based at least in part on the determination.

3. The computer-implemented method of claim 2, wherein determining that the healthcare claim transaction was denied based at least in part on the product being an over-the-counter product not covered by the claims processor comprises:
    identifying a rejection message included in the received response; and
    determining, based at least in part upon the identified rejection message, that the healthcare claim transaction was denied based at least in part on the over-the-counter product not being covered by the claims processor.

4. The computer-implemented method of claim 1, wherein determining the classification of the product requested by the customer comprises:
    identifying a product identifier associated with the product;
    determining, based at least in part upon the product identifier, the classification of the product; and
    determining that the classification identifies the product as the over-the-counter product.

5. The computer-implemented method of claim 1, further comprising:
    calculating at the service provider computer a price for the product requested by the customer; and
    modifying the approved claim response at the service provider computer to include the calculated price.

6. The computer-implemented method of claim 5, wherein calculating a price for the product requested by the customer comprises:
- identifying one or more pricing parameters for the product;
- determining a quantity associated with the product; and
- calculating, at the service provider computer, the price based at least in part upon the identified one or more pricing parameters and the determined quantity.

7. The computer-implemented method of claim 6, wherein identifying one or more pricing parameters comprises obtaining, with the service provider computer, pricing information from an external data source.

8. The computer-implemented method of claim 5, wherein calculating a price further comprises:
- identifying a discount available for the product requested by the customer; and
- calculating the price for the product requested by the customer based at least in part upon the identified discount.

9. The computer-implemented method of claim 5, wherein calculating a price further comprises:
- determining that funding is available to cover at least a portion of the price of the product requested by the customer; and
- calculating the price for the product requested by the customer based at least in part upon the determination that funding is available.

10. The computer-implemented method of claim 1, further comprising:
- storing a financial record associated with the conversion by the service provider computer of the denied claim response to the approved claim response.

11. A system, comprising:
- at least one memory operable to store computer-executable instructions; and
- at least one processor configured to access the at least one memory and execute the computer-executable instructions to:
  - receive, from a healthcare provider computer, a healthcare claim transaction associated with a product requested by a customer;
  - direct communication of the healthcare claim transaction from the system to a claims processor for adjudication;
  - receive, at the system from the claims processor, an adjudicated denied claim response for the healthcare claim transaction, wherein the adjudicated denied claim response indicates denial of any financial coverage for the healthcare claim transaction and wherein the adjudicated denied claim response is not transmitted to the healthcare provider computer;
  - determine a classification of the product requested by the customer, wherein the classification identifies the product as an over-the-counter product;
  - convert, at the system, based at least in part upon the determined classification of the product, the denied claim response received from the claims processor to an approved claim response, the approved claim response indicating approval of at least a portion of a price of the requested product; and
  - direct communication of the approved claim response to the healthcare provider computer.

12. The system of claim 11, wherein the at least one processor is further configured to execute the computer-executable instructions to:
- determine that the healthcare claim transaction was denied based at least in part on the over-the-counter product not being covered by the claims processor; and
- convert the denied claim response based at least in part on the determination.

13. The system of claim 12, wherein the at least one processor is further configured to execute the computer-executable instructions to:
- identify a rejection message included in the received response; and
- determine, based at least in part upon the identified rejection message, that the healthcare claim transaction was denied based at least in part on the over-the-counter product not being covered by the claims processor.

14. The system of claim 11, wherein the at least one processor is further configured to determine the classification of the product requested by the customer by executing the computer-executable instructions to:
- identify a product identifier associated with the product;
- determine, based at least in part upon the product identifier, the classification of the product; and
- determine that the classification identifies the product as the over-the-counter product.

15. The system of claim 11, wherein the at least one processor is further configured to execute the computer-executable instructions to:
- calculate a price for the product requested by the customer; and
- modify the approved claim response to include the calculated price.

16. The system of claim 15, wherein the at least one processor is further configured to execute the computer-executable instructions to:
- identify one or more pricing parameters for the product;
- determine a quantity associated with the product; and
- calculate the price based at least in part upon the identified one or more pricing parameters and the determined quantity.

17. The system of claim 16, wherein the one or more pricing parameters are obtained from an external data source.

18. The system of claim 15, wherein the at least one processor is further configured to execute the computer-executable instructions to:
- identify a discount available for the product requested by the customer; and
- calculate the price for the product requested by the customer based at least in part upon the identified discount.

19. The system of claim 15, wherein the at least one processor is further configured to execute the computer-executable instructions to:
- determine that funding is available to cover at least a portion of the price of the product requested by the customer; and
- calculate the price for the product requested by the customer based at least in part upon the determination that funding is available.

20. The system of claim 11, wherein the at least one processor is further configured to execute the computer-executable instructions to:
- direct storage of a financial record associated with the conversion of the denied claim response to the approved claim response.

* * * * *